Figure 1:
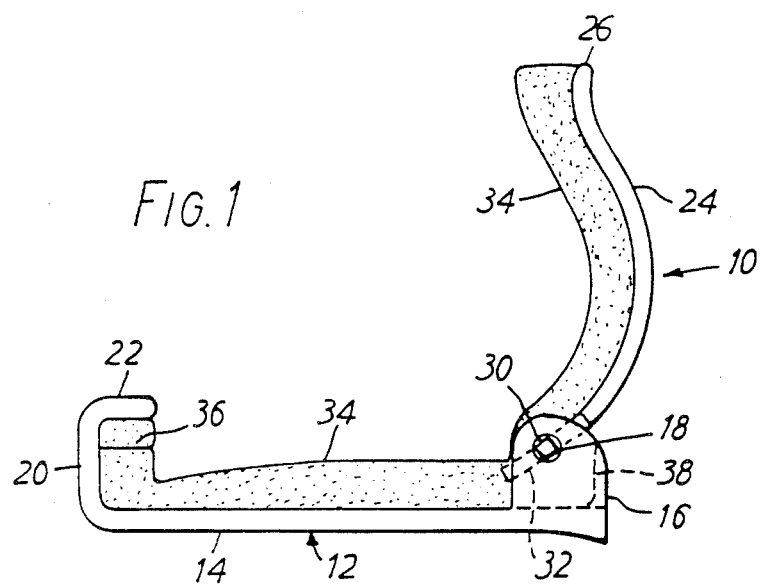

United States Patent [19]

Casey et al.

[11] Patent Number: 4,489,725
[45] Date of Patent: Dec. 25, 1984

[54] SEXUAL STERILIZATION DEVICES

[75] Inventors: Donn Casey, Cambridge; Gilbert M. Filshie, Nottingham, both of England

[73] Assignee: Simon Population Trust, Nottingham, England; a part interest

[21] Appl. No.: 464,766

[22] Filed: Feb. 7, 1983

[30] Foreign Application Priority Data

Feb. 11, 1982 [GB] United Kingdom ............... 8204011

[51] Int. Cl.³ ........................................... A61B 17/12
[52] U.S. Cl. ................................... 128/346; 128/325
[58] Field of Search ...................... 128/346, 325, 322; 24/460, 461, 462, 611, 499

[56] References Cited

U.S. PATENT DOCUMENTS 2,215,725  9/1940  Martinson .................... 128/346 X
3,463,156  8/1969  McDermott .................... 128/325
4,112,951  9/1978  Holka et al. ................... 128/346

FOREIGN PATENT DOCUMENTS 1530282  10/1978  United Kingdom .

OTHER PUBLICATIONS

*British Journal of Obstetrics and Gynaecology*, Jun. 1981, vol. 88, pp. 655–662, "The Titanium/Silicon Rubber Clip for Female Sterilization", by G. M. Filshie, et al. The Scientific Proceedings of VIII Asian & Oceanic Congress of Obstetrics & Gynaecology, Melbourne, Australia, Oct. 25–31, 1981, pp. 300 and 301, "The Titanium/Silicone Rubber Clip for Female Sterilization".

*Primary Examiner*—Michael H. Thaler
*Attorney, Agent, or Firm*—Salter & Michaelson

[57] ABSTRACT

A sexual sterilization device has titanium jaws connected at a pivot and internally lined with resiliently compressible silicone rubber. This lining serves to ensure that the lumen of a Fallopian tube remains occluded even after devitalisation of the tube tissue. A stub formed on one jaw beyond the pivot engages the lining of the other jaw so urging the two jaws apart. This enables the device to be held easily in an applicator and permits preparatory opening and closing movements of the jaws to be made so facilitating positioning of the device.

5 Claims, 7 Drawing Figures

SEXUAL STERILIZATION DEVICES

This invention relates to sexual sterilization devices having jaws which may be clamped about the Fallopian tube or vas deferens to effect occlusion of the lumen thereof.

Such a device is described in British patent specification no. 1530282 where there is shown a sterilization device having metal jaws lined with silicone rubber. The lining is arranged to be in compression when the device is applied to the Fallopian tube, for example, so that the lining is able to expand slightly as the tissue of the tube devitalizes and contracts over a period of time. This expanding movement of the lining ensures that the lumen of the tube remains fully occluded; one important cause of failure in the devices used previously is thus removed.

It is an object of this invention to provide an improved sexual sterilization device, the application of which is simplified.

Accordingly, the present invention consists in a sexual sterilization device comprising first and second jaws hingedly connected at a pivot and adapted to be clamped together about a genital duct to effect occlusion thereof; a lining of resiliently compressible material provided at least on the first jaw, the lining being in compression when the jaws are clamped together about said duct; and a stub formed integrally with the second jaw at the opposite side of the pivot from the second jaw; engagement between the stub and the resilient lining of the first jaw serving to urge the jaws apart.

Advantageously, a latch formation is provided on one jaw engageable with a part of the other to lock the jaws together, said other jaw being curved away from said one jaw intermediate the latch formation and the hinged connection so that, upon application of clamping force to the device, the jaws are first brought together in a hinging movement substantially unhindered by the latch formation, following by a flattening movement of said other jaw driving said part thereof into engagement with the latch formation.

Preferably, the stub is embedded within the resilient lining of the first jaw.

Since the jaws are in this way urged positively apart, reopening of the jaws—where this is necessary—before the latch has been actuated is achieved simply by removing or reducing the clamping force. There is no need for the applicator actively to separate the two jaws. This considerably simplifies the design of the applicator and also facilitates its use. Further, advantage can be taken of the force urging the jaws apart to hold the device in the applicator.

It is a problem common to sexual sterilization devices comprising hingedly connected clamping jaws that there is a risk of the Fallopian tube or vas deferens being squeezed out of the device when the jaws are clamped together. One approach to dealing with this problem is to provide the jaws, or a lining carried on the jaws, with "backwardly" directed teeth but this is a relatively complex manufacturing operation and is not particularly effective.

It is an object of a further form of this invention to provide an improved sexual sterilization device in which the above mentioned problem is overcome.

Accordingly, the present invention consists in a further form in a sexual sterilization device comprising two hingedly connected jaws adapted to be clamped together about a genital duct to effect occlusion thereof and a lining of resiliently compressible material provided on opposing surfaces of the respective jaws, the lining being in compression when the jaws are clamped together about the duct, wherein the jaws and lining are so shaped and dimensioned that the point of latest contact between the lining of one jaw and the other moves toward the hinged connection as the jaws are clamped together.

Figure 2:
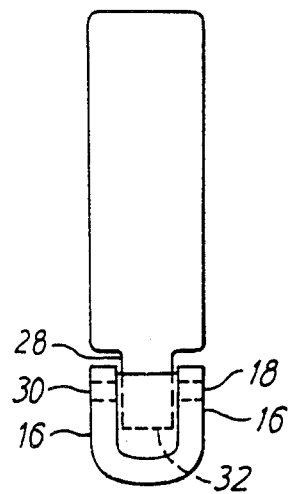

In this way, the duct is pushed into rather than out of the device as the jaws are clamped together. This invention will now be described by way of example with reference to the accompanying drawings in which:

FIG. 1 is a side elevation of a sexual sterilization device according to this invention, FIG. 2 is a rear elevation of the device shown in FIG. 1, and FIGS. 3(a) to (e) are views similar to FIG. 1 showing various stages in the application of the device to a Fallopian tube.

Referring first to FIGS. 1 and 2, the device is seen generally to comprise upper and lower jaws 10 and 12 respectively. In this example the jaws are formed of titanium.

The lower jaw 12 comprises a flat clamping portion 14 having a one end thereof two parallel and upstanding ears 16. Each ear has a smaller aperture 18 which provides a pivotal mounting for the upper jaw as will be described. At the opposite end of the clamping portion 14, the lower jaw is bent upwardly to provide a bight portion 20 which is generally perpendicular to the clamping portion and a latching portion 22 which is generally parallel to the clamping portion.

The upper jaw 10 has a central clamping portion 24 which is curved away from the lower jaw. The clamping portion terminates at the free end of the upper jaw in a lip 26 and at the opposite end of the jaw there is formed a portion 28 of reduced width. Two lugs 30 are provided on this portion 28, the lugs extending into the respective apertures 18 of the lower jaw. The portion 28 of reduced width extends beyond the lugs 30 to provide a stub 32.

As is shown in FIG. 1, the opposing surfaces of the jaws—as well as the interior surface of the latch formation comprising bight portion 20 and latch portion 22—are lined with resiliently compressible material. In this example, the material is a very soft room temperature vulcanising silicone rubber. The lining is applied by placing the assembled upper and lower jaws into a suitably shaped mould after a preparatory keying treatment of the surface to be lined. This preparatory treatment preferably includes blasting.

In the finished device, the lining 34 is of roughly uniform thickness over the curved portion 24 of the upper jaw and extends to the lip 26. There is a similar thickness of lining over the base portion 14 of the lower jaw and the lining can be seen to fill the pocket formed by the bight portion 20 and latch portion 22. For reasons to be explained, a slit 36 is cut into the lining in this pocket. In the region of the pivot formed by lugs 30 and apertures 18, the lining 34 extends between the ears 16 with the effect that the stub 32 is effectively embedded in the lining of the lower jaw. Behind the stub 32 and between the two ears 16, the lining can be seen to take the form of a resilient pad 38.

As the jaws are brought together by a pivoting movement, the stub 32 distorts the pad 38 causing it to bulge outwards and setting up tensile stresses in the lining.

The resilience of the lining 38 clearly resists such movement and is therefore effective in urging or biasing the upper jaw to the position shown in FIG. 1.

The manner in which the described device is applied to a Fallopian tube can now be described.

The device is loaded into a suitable applicator having clamping parts which may be moved to close the jaws of the device. The orientation which the device assumes in the applicator is selected so that a slight closing of the jaws is required before the device can be loaded. In this way, the biassing force applied by the pad 38 to the upper jaw tending to return it to the normal position shown in FIG. 1 can be utilised to hold the device in the applicator. Referring now to FIGS. 3(a) to (e) the device is first located on the Fallopian tube shown at 50. During this operation, the jaws of the device can be opened and partially closed as many times as is necessary with the biassing action of the pad 38 returning the jaws to the open position whenever the clamping force of the actuator is reduced. As can be seen from FIGS. 3(a) and (e) there is no contact between the lip 26 of the upper jaw and the latch portion 22 of the lower jaw so that this preparatory opening and closing movement is unhindered by the latch formation. The facility to open and partially close the device greatly assists in the correct placement of the device and, moreover, enables the device/applicator combination to be used almost as a pair of forceps to bring the Fallopian tube to a suitable location in the abdominal cavity.

Figure 3A:
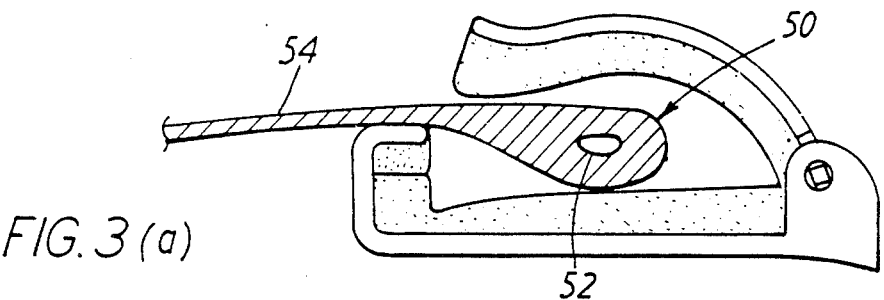
Figure 3B:
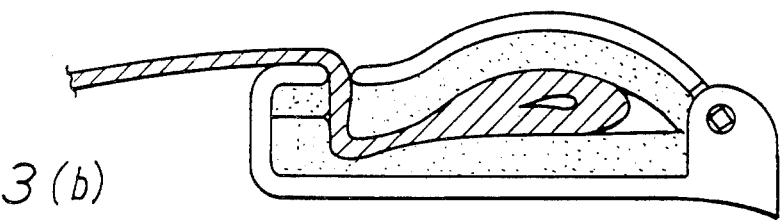
Figure 3C:
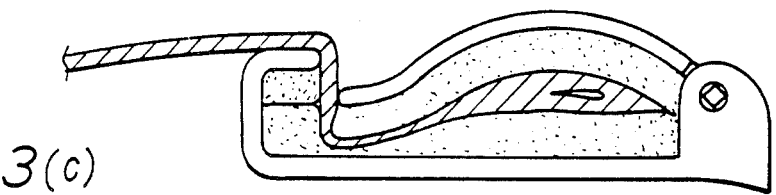
Figure 3D:
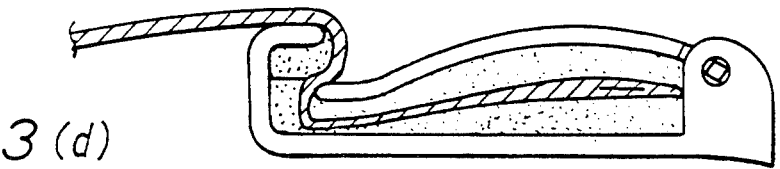
Figure 3E:
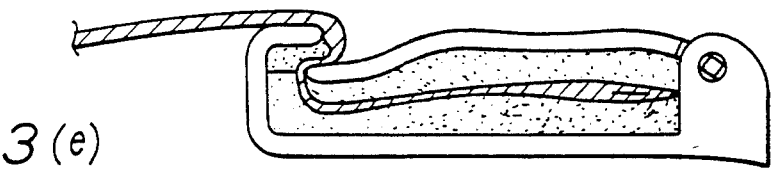

When the device has been correctly positioned, the clamping force applied by the applicator is increased until the position shown in FIG. (c) is reached with pivoting movement of the upper jaw substantially complete and the lining of the lower jaw in significant compression beneath the lip 26. At this stage, the lumen shown at 52 is partially occluded. The mesosalpinx shown at 54 is under compression beneath the lip 26 of the top jaw but it should be noted that there is no compression of the mesosalpinx between metal parts. With a further increase in the clamping force, the upper jaw starts to undergo a deformation which consists essentially of a flattening of the curved portion 24. This deformation drives the lip 26 into the pocket beneath the latch formation 22 until the position shown in FIG. 3(e) is reached with the upper jaw substantially flat. It should here be noted that because the lining extends over the inner surface of the latch portion 22, the mesosalpinx is effectively cushioned and still suffers no direct compression between metal parts. In consequence the risk of bleeding from the vessels of the mesosalpinx is much reduced.

The lip 26 is positively held or latched beneath the latch portion 22 and this, coupled with the permanent deformation undergone by the upper jaw, serves to ensure that there is no relaxation in the clamping action of the jaws. In the clamped device, the lining, which is of course resiliently compressible, has undergone a significant compression so that when the tissue of the Fallopian tube devitalises and contracts, the lining is able to expand slightly so ensuring that the lumen remains fully occluded.

A further feature of the described device is that because of the thickness selected for the lining 34, the contour of the upper jaw 10 and the separation between the apertures 18 and the base portion 14 of the lower jaw, the initial contact as the jaws are brought together is made towards the free end of the jaws, the point of latest contact thereafter moving toward the pivot or hinge as the clamping force applied to the device is steadily increased. As a consequence, the Fallopian tube—once gripped by the jaws—is forced towards the hinge or pivot when the clamping force is increased. This can be seen quite clearly in the sequence of FIGS. 3(a) to (c). The likelihood of the tube being squeezed out of the device is thus significantly reduced.

A device according to this invention for male sterilization will be smaller than that described but otherwise substantially the same. The method of applying the device to the vas deferens is analogous to that described for the Fallopian tube.

This invention has been described by way of example only and a variety of modifications are possible without departing from the scope of the invention. The materials described are those preferred but alternatives are possible provided, of course, that they are tissue compatible. Thus the jaws could for example be formed of tantalum.

In other modifications, the bight portion 20 and latch portion 22 of the lower jaw could be replaced by a different latch formation. Similarly, the described pivot arrangement could take a variety of other forms and could, indeed, be replaced by a hinge piece formed integrally with both the upper and lower jaws. Such a modification is not, however, preferred since it would not readily permit the preparatory opening and closing movements of the device, the advantages of which have been described above.

What is claimed is:

1. A sexual sterilization device comprising a first jaw, a second jaw hingedly connected to said first jaw at a pivot, a resiliently compressible lining on said first jaw, said first and second jaws being hingeable to a clamping position for clamping a genital duct therebetween to effect the occlusion of said genital duct, said lining being in compression when said jaws are in said clamping position, and a stub attached to said second jaw and extending a distance therefrom on the opposite side of said pivot from said second jaw, said stub being engageable with said lining to resiliently bias said first and second jaws apart.

2. A device according to claim 1, wherein a latch formation is provided on one jaw engageable with a part of the other to lock the jaws together, said other jaw being curved away from said one jaw intermediate the latch formation and the hinged connection so that, on application of clamping force to the device, the jaws are first brought together in a hinging movement substantially unhindered by the latch formation, followed by a flattening movement of said other jaw driving said part thereof into engagement with the latch formation.

3. A device according to claim 1 wherein said stub is embedded within the resilient lining of the first jaw.

4. A sexual sterilization device comprising first and second jaws hingedly connected at a pivot and adapted to be clamped together about a genital duct to effect occlusion thereof; a lining of resiliently compressible material provided at least on the first jaw, the lining being in compression when the jaws are clamped together about said duct; and stub means formed integrally with one jaw at the opposite side of the pivot from said one jaw for engaging part of said lining and imparting tensile strain thereto upon clamping movement of the jaws, tensile forces in said part thereby serving to urge said jaws apart.

5. A sexual sterilization device comprising:

a. a first jaw having a clamping portion and pivot means defining a pivot axis;
b. a second jaw having a clamping portion and being hingedly connected to said first jaw at said pivot means, the jaws being adapted to be clamped together about a genital duct to effect occlusion therewith;
c. A lining of resiliently compressible material provided on the clamping portion of at least the first jaw and being in compression when the jaws are clamped together about a duct, the said lining extending beyond the pivot axis on the fist jaw to define a resilient pad;
d. a stub formed integrally with the second jaw at the opposite side of the pivot axis from the clamping portion, the stub being embedded in said resilient pad such that after an initial closing movement of the jaws, the resilience in said pad acting on the stub of the second jaw serves to return the jaws to a fully open position.

* * * * *